United States Patent
Högnelid

[11] Patent Number: 6,112,744
[45] Date of Patent: *Sep. 5, 2000

[54] THERAPEUTIC SYSTEM FOR RESPIRATORY CARE WITH A LIQUID AND GAS WITH AN OSCILLATOR DEVICE FOR PROMOTING EXCHANGE BETWEEN THE GAS AND LIQUID

[75] Inventor: Kurt Högnelid, Bromma, Sweden

[73] Assignee: Siemens Elema AB, Solna, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/992,183

[22] Filed: Dec. 17, 1997

[30] Foreign Application Priority Data

Dec. 20, 1996 [SE] Sweden .................... 9604724

[51] Int. Cl.[7] .......................... A61N 15/00; A61N 16/00; A62B 18/00; A62B 7/00; A62B 9/00
[52] U.S. Cl. ............... 128/200.24; 128/913; 128/202.15; 128/201.21
[58] Field of Search .................. 128/200.24, 201.21, 128/913, 207.15

[56] References Cited

U.S. PATENT DOCUMENTS

| | | | |
|---|---|---|---|
| 5,029,580 | 7/1991 | Radford et al. | 128/207.14 |
| 5,158,536 | 10/1992 | Sekins et al. | 604/20 |
| 5,307,794 | 5/1994 | Rauterkus et al. | 128/200.24 |
| 5,437,272 | 8/1995 | Fuhrman | 128/204.18 |
| 5,470,885 | 11/1995 | Fuhrman et al. | 128/204.18 |
| 5,540,225 | 7/1996 | Schutt | 128/207.15 |
| 5,546,608 | 8/1996 | Sekins et al. | 604/20 |
| 5,707,352 | 1/1998 | Sekins et al. | 604/56 |
| 5,788,665 | 8/1998 | Sekins | 604/19 |

FOREIGN PATENT DOCUMENTS

| | | |
|---|---|---|
| WO 93/09833 | 5/1993 | WIPO . |
| WO 96/22052 | 7/1996 | WIPO . |

OTHER PUBLICATIONS

"High–Frequency Oscillatory Ventilation with Partial Liquid Ventilation in a Model of Acute Respiratory Failure," Baden et al., Crit Care Med., vol. 25, No. 2, (1977) pp. 299–302.

*Primary Examiner*—John G. Weiss
*Assistant Examiner*—Joseph F. Weiss, Jr.
*Attorney, Agent, or Firm*—Hill & Simpson

[57] ABSTRACT

In respiratory care with liquids, the patient is connected to a liquid apparatus and a ventilator for supplying and removing a treatment liquid and a breathing gas respectively to/from the patient. The exchange of gases between the breathing gas and the treatment liquid is improved with a device which causes the breathing gas and/or the liquid to oscillate. The device may be a breathing gas generator which generates different frequencies to cause the breathing gas and treatment liquid to oscillate at appropriate frequencies. The device may be a vibrator unit which is applied to the chest to cause the treatment liquid to oscillate. The device may be a magnetic field generator for generating a magnetic field across the lungs and setting electrically conductive components in the treatment liquid in motion.

8 Claims, 1 Drawing Sheet

THERAPEUTIC SYSTEM FOR RESPIRATORY CARE WITH A LIQUID AND GAS WITH AN OSCILLATOR DEVICE FOR PROMOTING EXCHANGE BETWEEN THE GAS AND LIQUID

BACKGROUND OF THE INVENTION

1. Field of the Invention

The present invention relates to a device for use in a therapeutic system for respiratory care with a liquid of the type wherein a lung is partially filled with a special treatment liquid, and a ventilator supplies breathing gas to portions of the lung which are not filled with the treatment liquid, so that a gas exchange occurs between the breathing gas and the treatment liquid.

2. Description of the Prior Art

Respiratory treatment with liquid has proved to be effective, especially for severely ill or injured patients or in cases of pulmonary immaturity. In treatment with liquid, the damaged parts of lungs are filled with a special treatment liquid, usually a perfluorocarbonate. The liquid spreads to the alveoli and keeps them distended. Oxygen, for example, is highly soluble in the liquid, and gas is exchanged between the blood system and liquid in the alveoli. A breathing gas can simultaneously be supplied to the parts of the lungs (including the entire respiratory system, i.e. bronchi and other airways), in order to add fresh oxygen to the liquid and remove carbon dioxide. One such treatment system is described in PCT Application WO 93/09833.

Since the area of contact between the treatment liquid and breathing gas can be relatively small, especially on occasions in which a relatively large volume of liquid is employed, improving the exchange of gas between the treatment liquid and the breathing gas is desirable.

SUMMARY OF THE INVENTION

An object of the present invention is to provide a device for use in liquid ventilation systems which improves gas exchange between the treatment liquid and the breathing gas.

The above object is achieved in accordance with the principles of the present invention in a device for use in a therapeutic system for respiratory care of a subject, wherein a special treatment liquid is supplied to a lung so as to at least partially fill the lung and a ventilator supplies breathing gas to the portion of the lung which is not filled with the treatment liquid so that a gas exchange occurs between the breathing gas and the liquid, the device causing the breathing gas and/or the treatment liquid to oscillate so as to increase and promote gas exchange between the breathing gas and the treatment liquid.

When the treatment liquid and/or breathing gas is/are made to oscillate, gas exchange conditions are improved in the liquid/gas as well as in the gas/liquid interface area.

DESCRIPTION OF THE PREFERRED EMBODIMENTS

Figure 1:
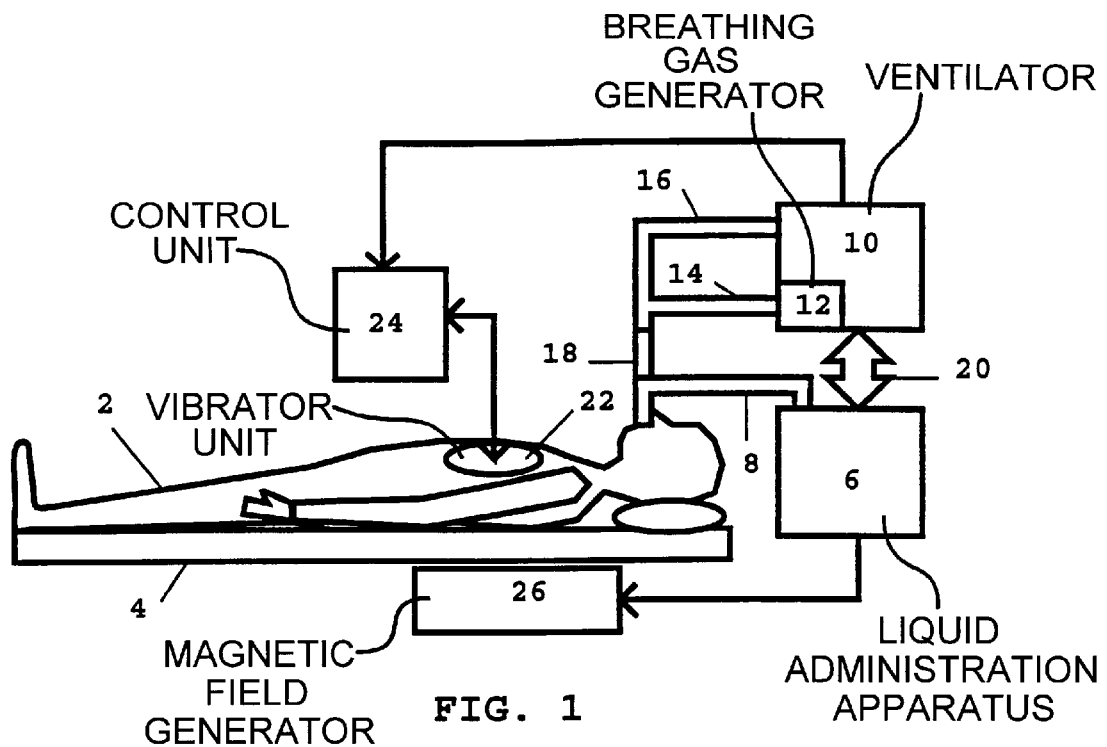
FIG. 1 shows one embodiment of a device according to the invention in a liquid treatment system connected to a patient.

FIG. 1 shows a patient 2 on a treatment couch 4. The patient 2 is connected to a liquid treatment administration apparatus 6 by a liquid tube 8. The liquid administration apparatus 6 contains a treatment liquid, such as a solution of perfluorocarbon, which can be delivered to the lungs of the patient 2 via the liquid tube 8. The lungs of the patient 2 can accordingly be wholly or partially filled with the treatment liquid.

A ventilator 10, equipped with a breathing gas generator 12, is also connected to the patient 2. A breathing gas can be fed to and evacuated from the patient 2 via an inspiratory tube 14 and an expiratory tube 16. The inspiratory tube 14 and expiratory tube 16 are connected to a patient tube 18, usually a tracheal tube. The breathing gas reaches the parts of the lung which are not filled with liquid.

Between the treatment liquid in the lungs and the blood system of the patient 2 there is an exchange of gases in which, primarily, oxygen diffuses into the blood system, and carbon dioxide diffuses into the treatment liquid. The carbon dioxide is subsequently carried by the treatment liquid to the treatment liquid-breathing gas interface. Gas exchange, in which carbon dioxide transfers to the breathing gas for evacuation from the patient 2, also takes place here, and oxygen in the breathing gas dissolves in the treatment liquid and is carried by same to the alveoli for delivery to the bloodstream.

Gas transport would be very slow if diffusion were the only mechanism for the transportation of gases in treatment liquid. A number of embodiments of a device for accelerating or improving gas exchange are described below.

In a first embodiment of the device the breathing gas generator 12 generates at least two breathing gas frequencies. One frequency is selected to maximize gas exchange in the breathing gas. This causes the rapid removal of carbon dioxide and rapid delivery of oxygen at the interface between the treatment liquid and breathing gas. In this way, a maximum difference in partial pressures is maintained between the two gases in the treatment liquid and breathing gas respectively. A big difference in partial pressure increases diffusion. The second frequency is selected to make the treatment liquid oscillate at an appropriate frequency. The transport of gas in the treatment liquid will then increase.

The two frequencies can either be generated as superimposed frequencies for simultaneous action on the breathing gas and treatment liquid or be generated as alternating frequencies for sequential action on the breathing gas and treatment liquid. A number of frequencies can also be used to increase the effect of gas exchange.

An alternative way of inducing the treatment liquid to oscillate at an appropriate frequency is illustrated in FIG. 1. A vibrator unit 22 is placed at an appropriate position on the chest of the patient 2. The vibrator unit 22 is regulated by a control unit 24 connected to the liquid treatment system via the ventilator 10. Vibrations from the vibrator unit 22 are transmitted to the treatment liquid in the lungs and cause it to oscillate. This accordingly creates a stirring effect which accelerates gas transport in the treatment liquid.

Another alternative way of inducing oscillations in the treatment liquid is shown in FIG. 1, with a magnetic field generator 26 placed under the patient 2. The magnetic field generator 26 generates a varying magnetic field across the lungs of the patient 2. The treatment liquid contains, or can be supplied with, conductive components which are acted on by the magnetic field and cause a stirring effect in the treatment liquid.

Both the vibrator unit 22 and the magnetic field generator 26 can be used with the multi-frequency gas generator 12, i.e., with utilization of a number of frequencies in the generation of the breathing gas.

Figure 2:
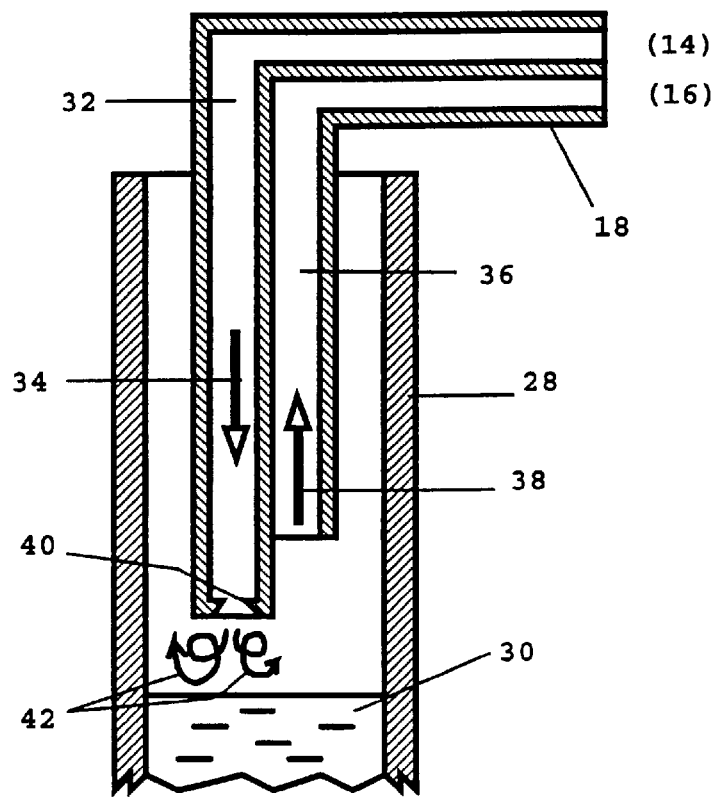
FIG. 2 shows an additional embodiment of a device according to the invention.

FIG. 2 shows a further embodiment of the device, viz. in the form of a specially devised tracheal tube 18. The tracheal tube 18 is shown inserted into the trachea 28, and the treatment liquid 30 is schematically depicted in order to illustrate the effect of the special design of the tracheal tube 18.

The tracheal tube 18 has a first lumen 32 for supplying breathing gas, as the arrow 34 indicates, and a second lumen 36 for evacuating breathing gas, as the arrow 38 shows. The first lumen 32 is therefore connected to the inspiratory tube 14, and the second lumen 36 is connected to the expiratory tube 16. A flange 40 is arranged at the lower end of the first lumen 32. The flange is designed to generate the greatest possible turbulence in breathing gas as the gas passes it. This is illustrated by the arrows 42.

The turbulent flow ensures that breathing gas is rapidly replaced in the area of the treatment liquid 30 interface. As noted above, this causes the difference in the partial pressures of the oxygen and carbon dioxide in the breathing gas and treatment liquid respectively to be as big as possible, thereby accelerating the exchange of gas in the interface area.

This effect is intensified when the breathing gas generator 12 (in FIG. 1) is devised to generate a constant flow of breathing gas through the first lumen 32 and second lumen 36 of the tracheal tube 18.

The specially designed tracheal tube 18 can be combined with all the aforesaid multi-frequency gas generator 12, vibrator unit 22 and magnetic field generator 26.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapeutic system for respiratory care of a subject, said system comprising:

means for administering a treatment liquid to a lung of a subject for at least partially filing a lung of a subject, including a treatment liquid source and a tube adapted for insertion in a subject via which said treatment liquid is administered;

a ventilator connected to said tube for supplying a breathing gas to a portion of a lung of a subject not filled with said treatment liquid, and thereby producing a non-physiological interface between said breathing gas and said treatment liquid with gas exchange occurring at said non-physiological interface; and oscillator means for causing at least one of said breathing gas and said treatment liquid to oscillate for increasing gas exchange between said breathing gas and said treatment liquid at said non-physiological interface in said tube.

2. A system as claimed in claim 1 wherein said oscillator means comprises a tracheal tube connected between said ventilator and a subject through which said breathing gas flows, said tracheal tube containing a first lumen through which breathing gas flows toward a subject and a second lumen in which breathing gas flows away from a subject, and means disposed at an end of said first lumen for causing turbulence in said breathing gas.

3. A system as claimed in claim 2 wherein said ventilator comprises a breathing gas generator which generates a continuous flow of breathing gas.

4. A system as claimed in claim 1 wherein said oscillator means comprises a breathing gas generator in said ventilator which generates a flow of breathing gas having at least two oscillation frequencies, a first of said oscillation frequencies being matched to said breathing gas for causing maximum gas exchange between said breathing gas and said treatment liquid, and a second of said oscillation frequencies being matched to said treatment liquid for causing said treatment liquid to oscillate to increase the speed of gas transport through said treatment liquid.

5. A system as claimed in claim 4 wherein said breathing gas generator comprises means for generating a flow of breathing gas with said oscillation frequencies being respectively superimposed therein.

6. A system as claimed in claim 4 wherein said breathing gas generator comprises means for generating a flow of breathing gas with said oscillation frequencies respectively alternating therein.

7. A system as claimed in claim 1 wherein said oscillator means comprises a vibrator unit adapted for application to a chest of a therefor subject for causing said treatment liquid to oscillate at a frequency which increases the transport of breathing gas through said treatment liquid.

8. A system as claimed in claim 1 further comprising at least one conductive component in said treatment liquid, and wherein said oscillator means comprises a magnetic field generator which generates a variable magnetic field across said treatment liquid.

* * * * *